(12) United States Patent
Litvak

(10) Patent No.: US 8,364,274 B1
(45) Date of Patent: Jan. 29, 2013

(54) SYSTEMS AND METHODS FOR DETECTING ONE OR MORE CENTRAL AUDITORY POTENTIALS

(75) Inventor: Leonid M Litvak, Los Angeles, CA (US)

(73) Assignee: Advanced Bionics, LLC, Valencia, CA (US)

( * ) Notice: Subject to any disclaimer, the term of this patent is extended or adjusted under 35 U.S.C. 154(b) by 246 days.

(21) Appl. No.: 11/962,508

(22) Filed: Dec. 21, 2007

Related U.S. Application Data

(60) Provisional application No. 60/877,773, filed on Dec. 29, 2006.

(51) Int. Cl.
*A61N 1/05* (2006.01)

(52) U.S. Cl. ............ 607/57; 607/55; 607/56; 607/137; 606/109; 623/10; 623/24; 623/25; 381/312

(58) Field of Classification Search .............. 607/55–57, 607/62; 623/10, 24–25; 606/109; 381/312
See application file for complete search history.

(56) References Cited

U.S. PATENT DOCUMENTS

| | | | | |
|---|---|---|---|---|
| 4,305,402 | A * | 12/1981 | Katims ...................... | 600/554 |
| 4,319,584 | A * | 3/1982 | McCall ...................... | 607/136 |
| 4,400,590 | A | 8/1983 | Michelson | |
| 4,532,930 | A | 8/1985 | Crosby et al. | |
| 4,592,359 | A | 6/1986 | Galbraith | |
| 4,819,647 | A | 4/1989 | Byers et al. | |
| 4,947,844 | A | 8/1990 | McDermott | |
| 4,966,164 | A * | 10/1990 | Colsen et al. ................... | 607/72 |
| 5,514,175 | A * | 5/1996 | Kim et al. ...................... | 607/136 |
| 5,626,629 | A * | 5/1997 | Faltys et al. .................... | 607/57 |
| 5,758,651 | A * | 6/1998 | Nygard et al. ................. | 600/554 |
| 5,824,022 | A * | 10/1998 | Zilberman et al. ............. | 607/57 |
| 6,129,753 | A | 10/2000 | Kuzma | |
| 6,157,861 | A * | 12/2000 | Faltys et al. .................... | 607/57 |
| 6,219,580 | B1 | 4/2001 | Faltys et al. | |
| 6,272,382 | B1 | 8/2001 | Faltys et al. | |
| 6,308,101 | B1 | 10/2001 | Faltys et al. | |
| 6,428,484 | B1 * | 8/2002 | Battmer et al. ............... | 600/554 |
| 7,137,946 | B2 * | 11/2006 | Waldmann ........................ | 600/25 |
| 2004/0138723 | A1 * | 7/2004 | Malick et al. .................... | 607/57 |
| 2005/0131272 | A1 * | 6/2005 | Waldmann ...................... | 600/25 |
| 2005/0137650 | A1 * | 6/2005 | Litvak et al. .................... | 607/57 |
| 2005/0251225 | A1 * | 11/2005 | Faltys et al. .................... | 607/57 |
| 2007/0250145 | A1 * | 10/2007 | Kraus et al. ................... | 607/136 |
| 2008/0195179 | A1 * | 8/2008 | Quick .............................. | 607/57 |

* cited by examiner

*Primary Examiner* — Niketa Patel
*Assistant Examiner* — Hiba El-Kaissi
(74) *Attorney, Agent, or Firm* — AdvantEdge Law Group, LLC

(57) ABSTRACT

Systems for detecting one or more central auditory potentials include an implantable cochlear stimulator configured to be implanted within a patient and to generate a stimulation current in accordance with one or more stimulation parameters, a signal processing unit configured to be located external to the patient and to be communicatively coupled to the implantable cochlear stimulator, and one or more electrodes configured to be removably coupled to the signal processing unit. The electrodes are configured to detect the one or more central auditory potentials and the signal processing unit is configured to process the detected central auditory potentials.

13 Claims, 5 Drawing Sheets

SYSTEMS AND METHODS FOR DETECTING ONE OR MORE CENTRAL AUDITORY POTENTIALS

RELATED APPLICATIONS

The present application claims priority under 35 U.S.C. §119(e) to U.S. Provisional Patent Application No. 60/877,773 by Leonid M. Litvak, filed on Dec. 29, 2006, and entitled "Systems and Methods for Detecting One or More Central Auditory Potentials," the contents of which are hereby incorporated by reference in their entirety.

BACKGROUND

The sense of hearing in human beings involves the use of hair cells in the cochlea that convert or transduce acoustic signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be helped by the use of conventional hearing aids that amplify sound so that acoustic signals reach the cochlea and the hair cells. Some types of conductive hearing loss may also be treated by surgical procedures.

Sensorineural hearing loss, on the other hand, is due to the absence or the destruction of the hair cells in the cochlea which are needed to transduce acoustic signals into auditory nerve impulses. Thus, people who suffer from sensorineural hearing loss are unable to derive any benefit from conventional hearing aid systems.

To overcome sensorineural hearing loss, numerous cochlear implant systems—or cochlear prosthesis—have been developed. Cochlear implant systems seek to bypass the hair cells in the cochlea by presenting electrical stimulation directly to the auditory nerve fibers. Direct stimulation of the auditory nerve fibers leads to the perception of sound in the brain and at least partial restoration of hearing function. To facilitate direct stimulation of the auditory nerve fibers, an array of electrodes may be implanted in the cochlea. A sound processor processes and translates an incoming sound into electrical stimulation pulses applied by these electrodes which directly stimulate the auditory nerve.

When a cochlear implant system is initially implanted in a patient, and during follow-up tests and checkups thereafter, it is usually necessary to fit the cochlear implant system to the patient. Such "fitting" includes adjustment of the base amplitude or intensity of the various stimuli generated by the cochlear implant system from the factory settings (or default values) to values that are most effective and comfortable for the patient. For example, the intensity or amplitude and/or duration of the individual stimulation pulses provided by the cochlear implant system may be mapped to an appropriate dynamic audio range so that the appropriate "loudness" of sensed audio signals is perceived. That is, loud sounds should be sensed by the patient at a level that is perceived as loud, but not painfully loud. Soft sounds should similarly be sensed by the patient at a level that is soft, but not so soft that the sounds are not perceived at all.

Hence, fitting and adjusting the intensity of the stimuli and other parameters of a cochlear implant system to meet a particular patient's needs requires the determination of a most comfortable current level (M). The most comfortable current level refers to a stimulation current level applied by a cochlear implant system at which the patient is most comfortable. The most comfortable current level (M) typically varies from patient to patient and from channel to channel in a multichannel cochlear implant.

Heretofore, the most comfortable current level (M) has been determined by an expert clinician presenting various stimuli to the patient and relying on subjective feedback from the patient as to how such stimuli are perceived. Such subjective feedback typically takes the form of either verbal (adult) or non-verbal (child) feedback. Unfortunately, relying on subjective feedback in this manner is difficult, particularly for those patients who may have never heard sound before and/or who have never heard electrically-generated "sound". For young children, the problem is exacerbated by a short attention span, as well as difficulty in understanding instructions and concepts, such as high and low pitch, softer and louder, same and different. Moreover, many patients, such as infants and those with multiple disabilities, are completely unable to provide subjective feedback.

In addition, the optimal fitting parameters of a cochlear implant system may vary during a patient's lifetime. For example, in the developing nervous system of young children, frequent changes in the intensity of the stimuli may be required in order to optimize the cochlear implant system. The optimal fitting parameters may vary during hormonal changes (e.g., a woman's menstrual cycle), or may vary with medication or illness. These changes may require frequent refitting sessions.

SUMMARY

Systems for detecting one or more central auditory potentials include an implantable cochlear stimulator configured to be implanted within a patient and to generate a stimulation current in accordance with one or more stimulation parameters, a signal processing unit configured to be located external to the patient and to be communicatively coupled to the implantable cochlear stimulator, and one or more electrodes configured to be removably coupled to the signal processing unit. The electrodes are configured to detect the one or more central auditory potentials and the signal processing unit is configured to process the detected central auditory potentials.

Methods of detecting one or more central auditory potentials include implanting a cochlear stimulator within a patient, providing a signal processing unit configured to be located external to the patient and communicatively coupled to the implantable cochlear stimulator, removably coupling one or more electrodes to the signal processing unit, detecting one or more central auditory potentials with the electrodes, and processing the detected central auditory potentials with the signal processing unit.

BRIEF DESCRIPTION OF THE DRAWINGS

The accompanying drawings illustrate various embodiments of the principles described herein and are a part of the specification. The illustrated embodiments are merely examples and do not limit the scope of the disclosure.

Throughout the drawings, identical reference numbers designate similar, but not necessarily identical, elements.

DETAILED DESCRIPTION

Figure 1:
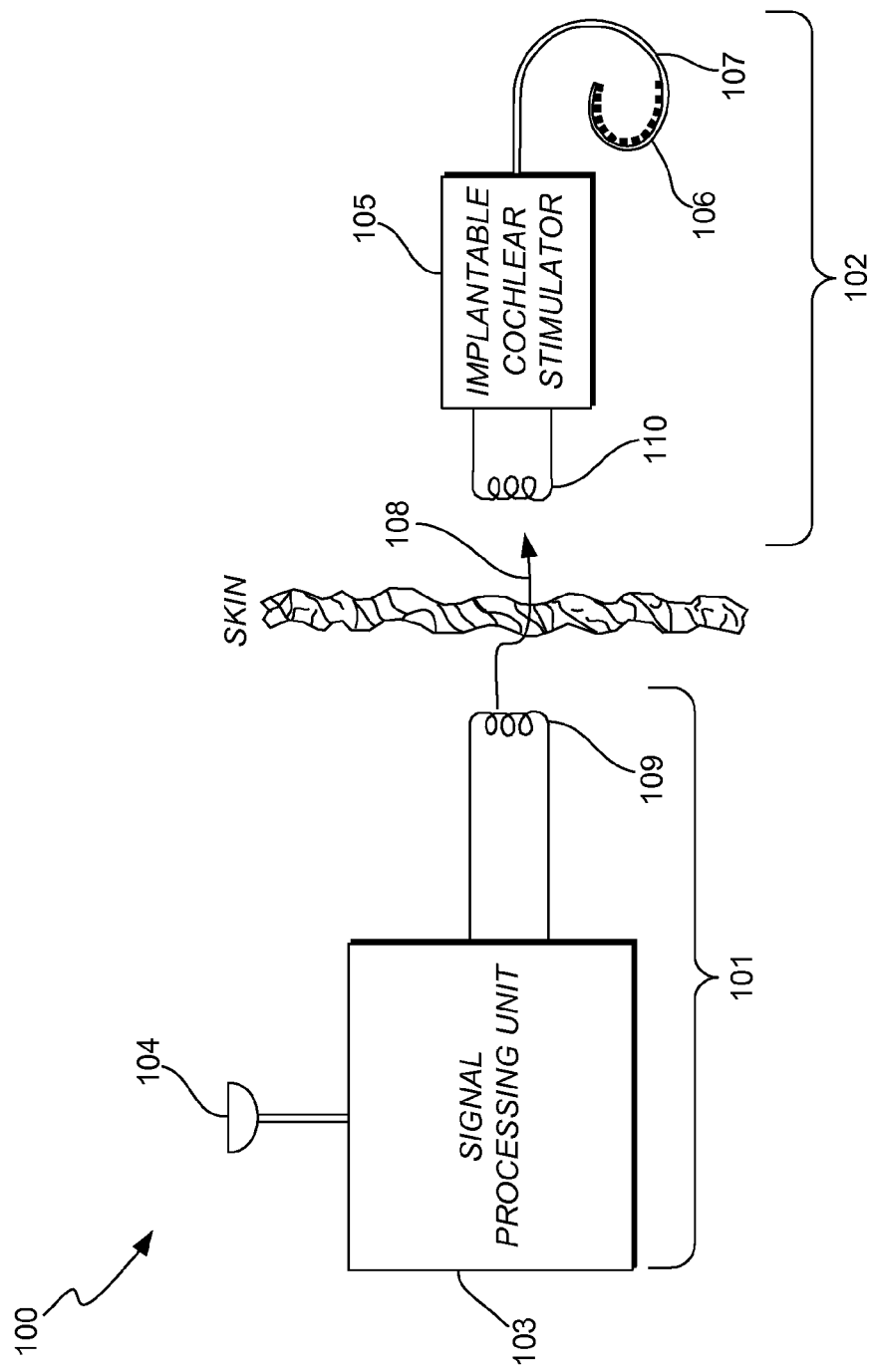
FIG. 1 illustrates an exemplary cochlear implant system according to principles described herein.

Systems and methods for detecting one or more central auditory potentials are described herein. An implantable cochlear stimulator configured to generate a stimulation current in accordance with one or more stimulation parameters is implanted within a patient. A signal processing unit configured to control the implantable cochlear stimulator is located external to the patient. To detect central auditory potentials, one or more electrodes are removably coupled to the signal processing unit. The electrodes are configured to detect one or more central auditory potentials and the signal processing unit is configured to process the detected central auditory potentials. In one implementation, the active electrode is placed on the vertex, while the reference and guard electrodes are placed on contralateral mastoid and forehead respectively.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

When neurons within auditory nerves are activated by natural or artificial means, they generate pulses of electrical current. These pulses are referred to as "action potentials." The current produced by a single neuron is very small, but artificial electrical stimulation applied by, for example, a cochlear implant system, tends to recruit large numbers of neurons synchronously. This results in a compound action potential (CAP) that can be recorded electronically in the tissues surrounding the neurons, particularly in the fluid-filled cochlear ducts where the stimulating electrodes of a cochlear implant system are usually located. The amplitude of the compound action potential is approximately related to the number of auditory neurons that have been activated by the electrical stimulation.

Action potentials produced by auditory neurons are conducted to various relay nuclei of the brainstem, which transform the information into action potentials that are transmitted by other neurons to yet further nuclei and eventually to the perceptual centers in the cerebral cortex. When the nerve signals finally arrive in the perceptual centers, they give rise to the conscious perception of sound and its apparent loudness.

Compound action potentials resulting from patterns of neural activity in these perceptual centers within the cerebral cortex can also be recorded electronically. For example, as will be described in more detail below, action potentials that occur within the cerebral cortex may be recorded by external electrodes that are attached to the outer surface of a patient's head. Such compound action potentials, as well as other compound action potentials that are generated by centers that are more central than the auditory nerve will be referred to herein as "central auditory potentials."

The presence of central auditory potentials reveals information about the auditory system and the functions of the auditory brainstem, and possibly reflects cognitive processing of auditory signals. Hence, it is often desirable during a cochlear implant system fitting session to measure one or more central auditory potentials in order to more effectively fit a cochlear implant system to a patient.

Conventional methods of measuring central auditory potentials involve the use of specialized equipment found in some clinicians' offices. However, such specialized equipment is not easily accessible to many patients and clinicians. Moreover, the use of such equipment on patients with cochlear implant systems may result in undesirable signal interference and noise artifacts.

Hence, systems and methods for effectively measuring central auditory potentials within cochlear implant patients are described herein. To facilitate an understanding of the methods and systems described herein, an exemplary cochlear implant system will be described in connection with FIG. 1. Exemplary cochlear implant systems suitable for use as described herein include, but are not limited to, those disclosed in U.S. Pat. Nos. 4,400,590; 4,532,930; 4,592,359; 4,947,844; and 5,824,022; 6,219,580; 6,272,382; and 6,308,101. All of these listed patents are incorporated herein by reference in their respective entireties.

As shown in FIG. 1, the cochlear implant system 100 includes an external signal processor portion 101 and an implanted cochlear stimulation portion 102. The signal processor portion 101 may include a signal processing unit 103, a microphone 104, and/or additional circuitry as best serves a particular application. The cochlear stimulation portion 102 may include an implantable cochlear stimulator (ICS) 105, a number of electrodes 106 disposed on a lead 107, and/or additional circuitry as best serves a particular application. The components within the signal processor portion 101 and the cochlear stimulation portion 102 will be described in more detail below.

The microphone 104 of FIG. 1 is configured to sense acoustic signals and convert the sensed signals to corresponding electrical signals. The electrical signals are sent to the signal processing unit 103 over an electrical or other suitable link. Alternatively, the microphone 104 may be connected directly to, or integrated with, the signal processing unit 103.

The signal processing unit 103 may include any combination of hardware, software, and/or firmware as best serves a particular application. For example, the signal processing unit 103 may include one or more processors, digital signal processors (DSPs), filters, memory units, etc.

In some examples, the signal processing unit 103 may be configured to process the converted acoustic signals in accordance with a selected speech processing strategy to generate appropriate control signals or stimulation parameters for controlling the ICS 105. These stimulation parameters may specify or define the polarity, frequency, magnitude or intensity, location (i.e., which electrode pair or electrode group receive the stimulation current), and timing (i.e., when the stimulation current is to be applied to a particular electrode pair) of the stimulation current that is generated by the ICS 105.

It will be recognized that the signal processing unit 103 shown in FIG. 1 is merely illustrative of the many different signal processing units that may be used in connection with the present systems and methods. For example, the signal processing unit 103 may include a behind-the-ear (BTE) unit configured to be positioned behind the ear. Alternatively, the signal processing unit 103 may include a portable speech processor (PSP) device, a conventional hearing aid, or any other type of signal processing unit.

The lead 107 of FIG. 1 is adapted to be inserted within a duct of a patient's cochlea. As shown in FIG. 1, the lead 107 includes a multiplicity of electrodes 106 disposed along its length. The lead 107 may be substantially as shown and described in U.S. Pat. No. 4,819,647 or 6,129,753, each of which is incorporated herein by reference in its respective entirety. It will be recognized that any number of electrodes 106 may be disposed along the lead 107 as may best serve a particular application.

Each of the electrodes 106 is electrically coupled to the ICS 105. Electronic circuitry within the ICS 105 may therefore be configured to apply stimulation current to selected pairs or groups of electrodes 106 in accordance with a specified stimulation pattern controlled by the signal processing unit 103.

As mentioned, the ICS 105 and lead 107 may be implanted within the patient while the signal processing unit 103 and the microphone 104 are configured to be located outside the patient, e.g., behind the ear. Hence, the ICS 105 and the signal processing unit 103 may be transcutaneously coupled via a suitable data or communications link 108. The communications link 108 allows power and control signals to be sent from the signal processing unit 103 to the ICS 105. In some embodiments, data and status signals may also be sent from the ICS 105 to the signal processing unit 103.

The external and implantable portions of the cochlear implant system 100 may each include one or more coils configured to transmit and receive power and/or control signals via the data link 108. For example, the external portion 101 of the cochlear implant system 100 may include an external coil 109 and the implantable portion of the cochlear implant system 102 may include an implantable coil 110. The external coil 109 and the implantable coil 110 may be inductively coupled to each other, thereby allowing data and power signals to be wirelessly transmitted between the external portion and the implantable portion of the cochlear implant system 100.

Figure 2:
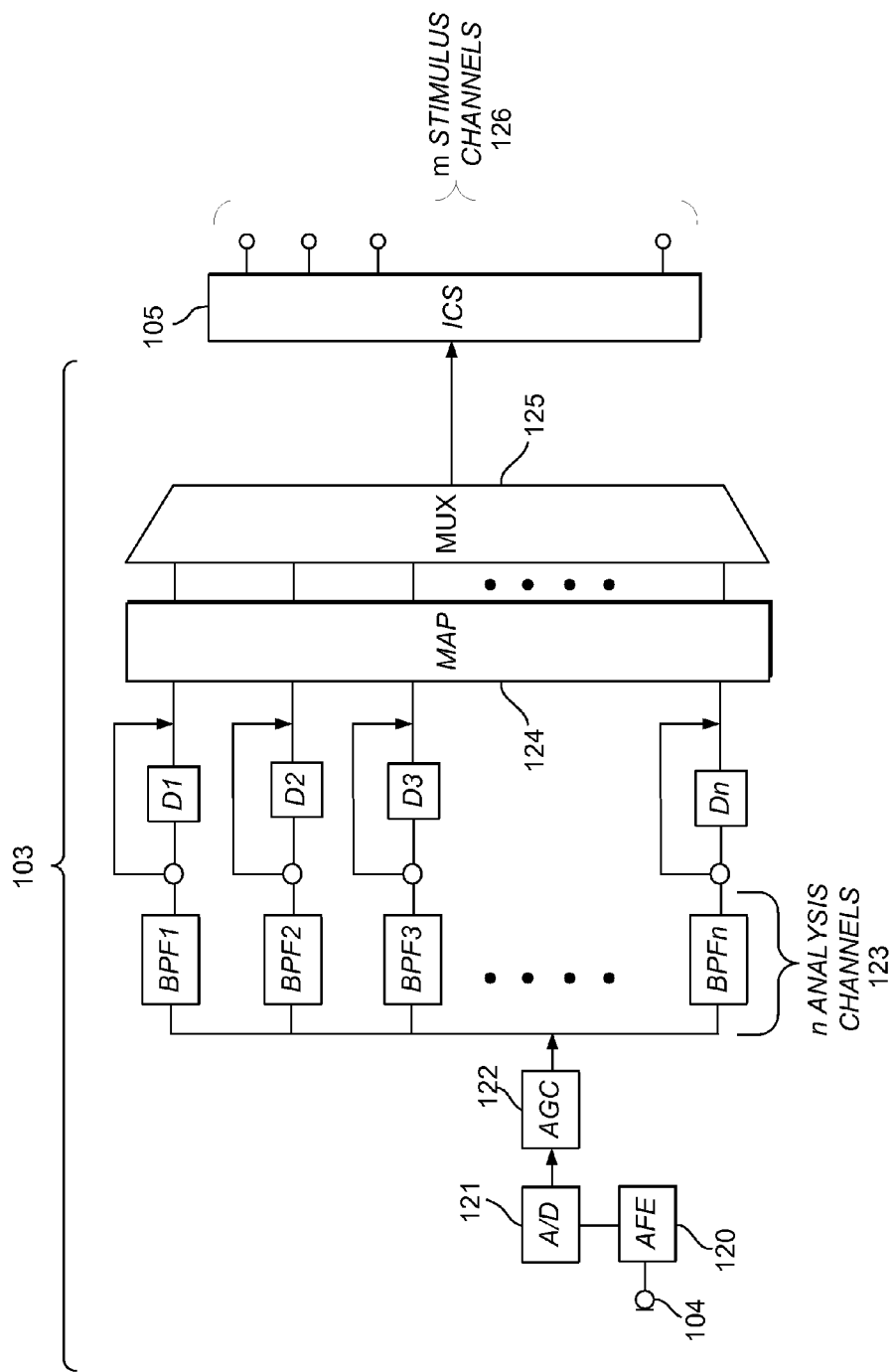
FIG. 2 is a functional block diagram of an exemplary signal processing unit and an exemplary implantable cochlear stimulator according to principles described herein.

FIG. 2 is a functional block diagram of the exemplary signal processing unit 103 and ICS 105. The functions shown in FIG. 2 are merely representative of the many different functions that may be performed by the signal processing unit 103 and/or the ICS 105.

As shown in FIG. 2, audio front-end (AFE) circuitry 120 is communicatively coupled to the microphone 104. This AFE circuitry 120 is configured to amplify an acoustic signal sensed by the microphone 104. The amplified acoustic signal is then converted to a digital signal by an analog-to-digital (A/D) converter 121. The resulting digital signal is then subjected to automatic gain control using a suitable automatic gain control (AGC) function 122.

After appropriate automatic gain control, the digital signal is then processed in one of a number of digital signal processing or analysis channels 123. For example, the signal processing unit 103 may include, but is not limited to, eight analysis channels 123. Each analysis channel 123 may respond to a different frequency content of the sensed acoustical signal. In other words, each analysis channel 123 includes a band-pass filter (BP1-BPFn) or other type of filter such that the digital signal is divided into n frequency channels. The lowest frequency filter may be a low-pass filter, and the highest frequency filter may be a high-pass filter.

As shown in FIG. 2, each analysis channel 123 may also include a detection stage (D1-Dn). Each detection stage (D1-Dn) may include an energy detection circuit (not shown), which may be realized, e.g., through a rectification circuit followed by an integrator circuit. As shown in FIG. 2, each of the detection stages (D1-Dn) may alternatively be bypassed depending on the particular signal processing strategy being used.

After energy detection, or bypassing of such, the signal from each of the n analysis channels 123 is forwarded to a mapping stage 124. The mapping stage 124 may be configured to map the signals in each of the analysis channels 123 to one or more of m stimulus channels 126. The mapping stage 124 may be further configured to perform additional processing of the signal, such as signal compression. The signals output by each analysis channel 123 may then be serialized by a multiplexer 125 into a single serial data channel and input into the ICS 105 to control the actual stimulus patterns that are applied to the patient via one or more of the electrodes 106.

In some examples, one or more external electrodes configured to sense or measure one or more central auditory potentials may be removably coupled to the signal processing unit 103. As will be described in more detail below, one or more of the components contained within the signal processing unit 103 may be configured to additionally process the sensed central auditory potentials. In this manner, a cochlear implant system may be more easily and conveniently fitted to a patient.

Figure 3:
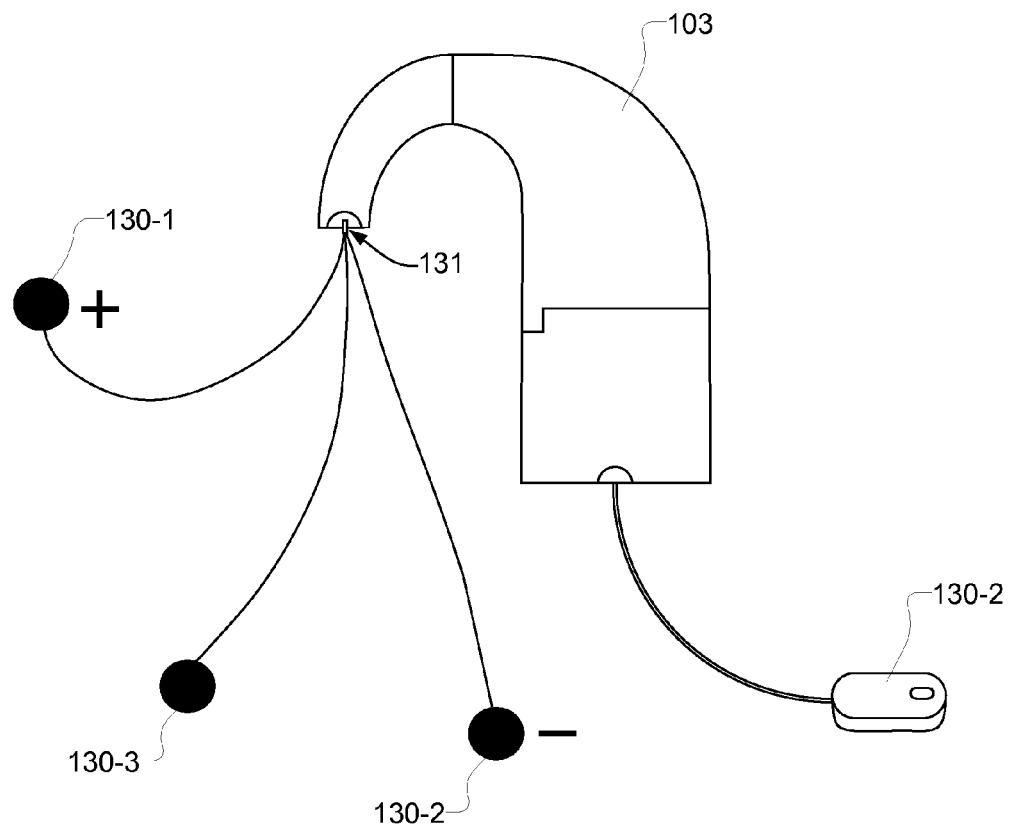
FIG. 3 illustrate an exemplary signal processing unit with three external electrodes coupled thereto according to principles described herein.

FIG. 3 illustrate an exemplary signal processing unit 103 with three external electrodes (130-1 through 130-3, collectively referred to as "electrodes 130") coupled thereto. The signal processing unit 103 shown in FIG. 3 is shaped like a BTE processing unit for illustrative purposes only. It will be recognized that the signal processing unit 103 may additionally or alternatively include any other type of signal processing unit as best serves a particular application.

In some examples, the signal processing unit 103 may be coupled to a headpiece 132, as shown in FIG. 3. The headpiece 132 may be configured to be coupled to the outer surface of a patient's head and may include the external coil 109 and/or any other component of the cochlear implant system 100 as may serve a particular application.

As mentioned, the electrodes 130 may be removably coupled to the signal processing unit 103. Hence, in some examples, the signal processing unit 103 may include a port 131 and/or other receiving means configured to communicatively couple to the electrodes 130. The port 131 may be located at any suitable location within the signal processing unit 103.

In some examples, the external electrodes 130 include an active (+) electrode 130-1, a reference (−) electrode 130-2, and a guard or common electrode 130-3. In this manner, the electrodes 130 may be placed at various locations on the head of the patient and used to sense or measure one or more central auditory potentials. It will be recognized, however, that the external electrodes 130 may include any number and/or type of electrode as best serves a particular application.

As mentioned, one or more components within the signal processing unit 103 may be configured to process central auditory potentials detected by the electrodes 130. For example, front end circuitry 120 may be configured to amplify the detected central auditory potentials and analog-to-digital converter 121 may be configured to convert the central auditory potentials to digital representations. One or more processors and/or other components included within the signal processing unit 103 may be configured to further process the central auditory potentials and fit the cochlear implant system to the patient by adjusting the stimulation parameters accordingly.

Active circuitry configured to cancel noise artifacts may also be included within the signal processing unit 103. Such circuitry may include, but is not limited to, one or more filters, processors, blanking circuits, impedance balancing circuits and/or amplifiers. Because these circuits may not be useful during the sound processing function, an alternative design would be to include these circuits within the electrode attachment 131. In this manner, artifacts may be effectively removed from the central auditory potentials—thereby improving the effectiveness of the fitting session.

In some examples, measurement of the central auditory potentials may be synchronized with delivery of stimulus to the cochlea. To illustrate, the signal processing unit 103 may be configured to measure the central auditory potentials during periods of time when stimulation is not being delivered to the cochlea. In this manner, artifact coupling into the signal path of the signal processing unit 103 may be avoided. Additionally or alternatively, the timing of various components within the signal processing unit 103 may be synchronized to minimize artifact coupling. For example, the sampling of one or more analog-to-digital converters within the signal processing unit 103 may be synchronized with the forward transmission of data to the implanted cochlear stimulator and with stimulation.

Hence, a patient's central auditory potentials may be more easily and effectively measured with the systems and methods described herein. Instead of using a dedicated external device to measure the central auditory potentials, a clinician or other operator may couple the electrodes 130 to the signal processing unit 103 and use the circuitry contained within the signal processing unit 103 to detect and process the central auditory potentials. The signal processing unit 103 may then use the results of the measurements to effectively adjust the stimulation parameters of the cochlear implant system 100. In some alternative examples, the signal processing unit 103 may be configured to store the results of the measurements within a data storage unit (e.g., a hard drive, programmable memory unit, etc.). The results may then be used at a later time to adjust the stimulation parameters of the cochlear implant system 100.

In some examples, a fitting station may additionally or alternatively be coupled to the signal processing unit 103. The fitting station may be used by a clinician, for example, to fit a cochlear implant system to a patient. Moreover, data acquired by the electrodes 130 may be viewed via the fitting station.

Figure 4:
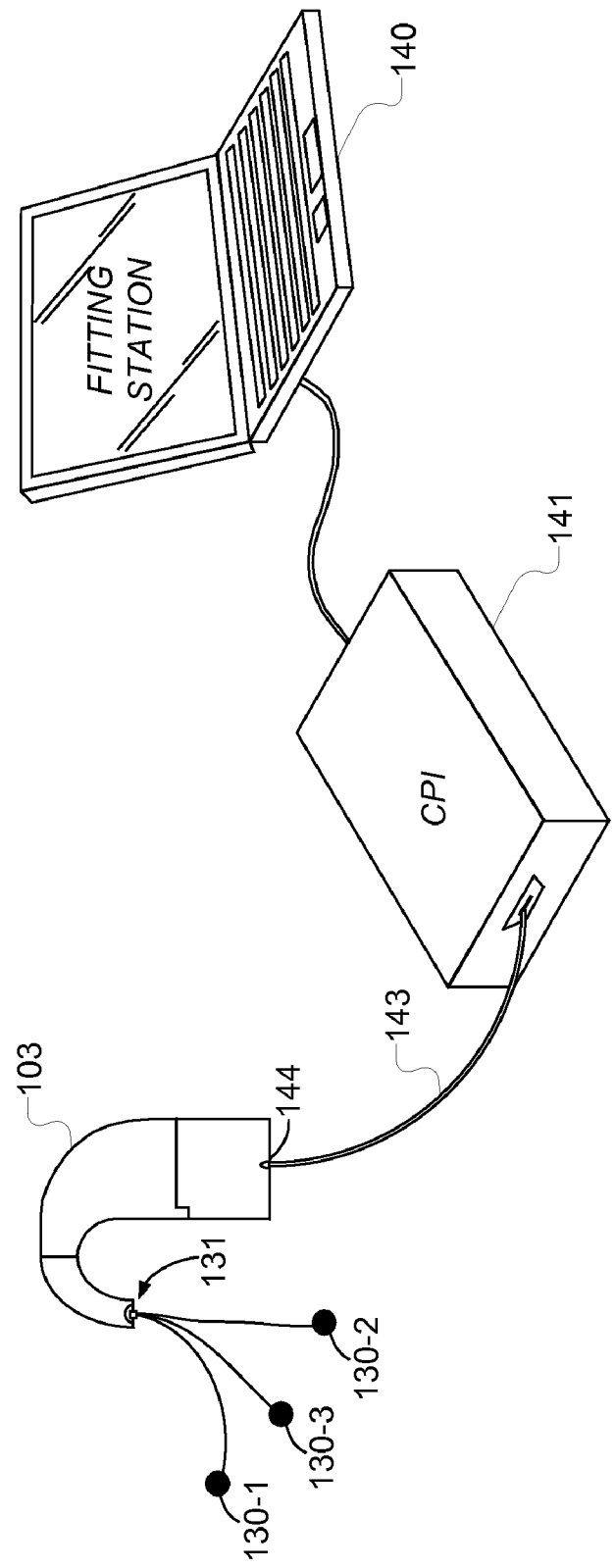
FIG. 4 illustrates an exemplary configuration wherein the signal processing unit is communicatively coupled to a fitting station according to principles described herein.

To this end, the signal processing unit 103 may additionally or alternatively be configured to communicate with a fitting station. For example, FIG. 4 illustrates an exemplary configuration wherein the signal processing unit 103 is communicatively coupled to a fitting station 140 via a clinician's programming interface (CPI) 141. The fitting station 140 may include a personal computer, hand held device, programming station, or any other type of device configured to control the operation of the signal processing unit 103. The CPI 141 is a device that allows the fitting station 140 to interface with the signal processing unit 103.

As shown in FIG. 4, a programming cable 143 may be used to communicatively couple the CPI 141 and fitting station 140 to the signal processing unit 103. To this end, the signal processing unit 103 may include a port 144 and/or other receiving means configured to communicatively couple to the programming cable 143.

Figure 5:
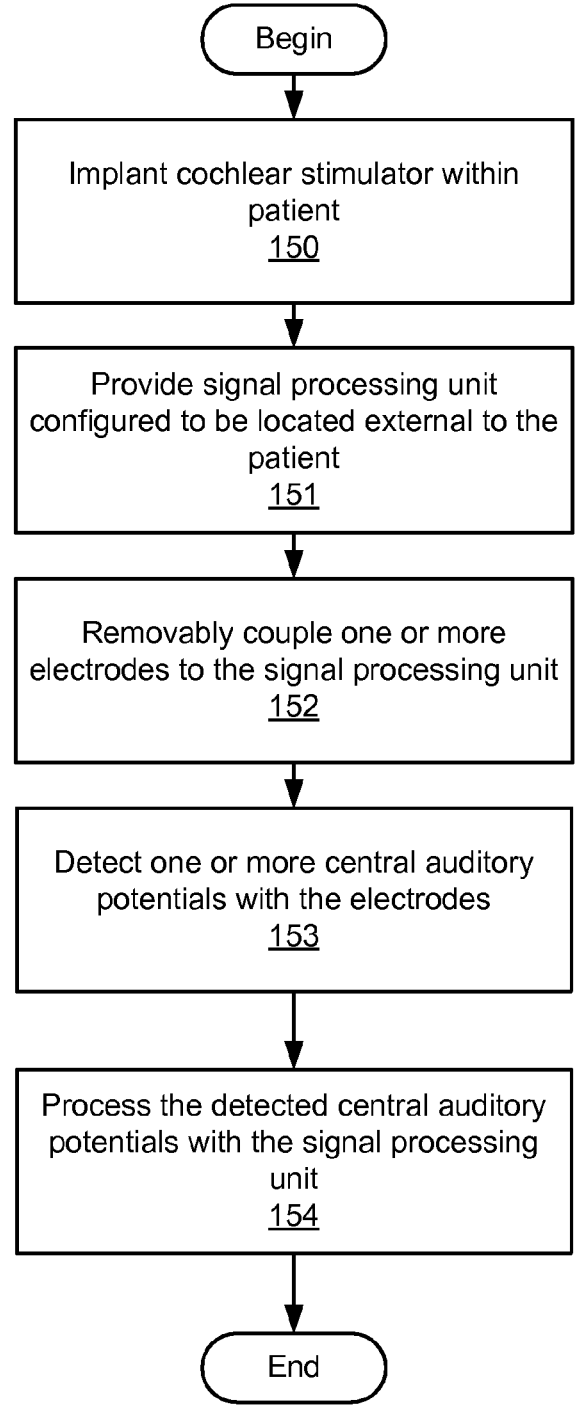
FIG. 5 is a flow chart illustrating an exemplary method of detecting one or more central auditory potentials according to principles described herein.

FIG. 5 is a flow chart illustrating an exemplary method of detecting one or more central auditory potentials. The steps shown in FIG. 5 are merely exemplary and may be modified, reordered, and/or added to as best serves a particular application.

In step 150, a cochlear stimulator is implanted within a patient using any suitable implantation technique. The cochlear stimulator is configured to generate and apply electrical stimulation to the cochlea and/or to any other location within the ear. A signal processing unit configured to be located external to the patient is also provided, as shown in step 151. The signal processing unit may be configured to communicate transcutaneously with the implanted cochlear stimulator.

To detect central auditory potentials, one or more electrodes may be removably coupled to the signal processing unit, as shown in step 152. The electrodes may then be used to detect one or more central auditory potentials, as shown in step 153. In step 154, the detected central auditory potentials may be processed by circuitry contained within the signal processing unit. In some examples, the same circuitry that is used to process the central auditory potentials may be used to process one or more acoustic signals detected by a microphone that is a part of the signal processing unit. Additionally or alternatively, the detection of the central auditory potentials may be synchronized with the generation of stimulation current.

The systems and methods described herein may be generally used in connection with any type of implantable stimulator and is not limited to use with implantable cochlear stimulators only. For example, the systems and methods described herein may be used in connection with deep brain stimulators, spinal cord stimulators, and/or any other type of implantable stimulator as best serves a particular application.

The preceding description has been presented only to illustrate and describe embodiments of the invention. It is not intended to be exhaustive or to limit the invention to any precise form disclosed. Many modifications and variations are possible in light of the above teaching.

What is claimed is:

1. A system for detecting one or more central auditory potentials, said system comprising:
   an implantable cochlear stimulator configured to be fully implanted within a patient and to generate and apply a stimulation current by way of one or more electrodes implanted within a cochlea of said patient in accordance with one or more stimulation parameters;
   a signal processing unit housed within a single casing and configured to be located external to said patient and communicatively coupled to said implantable cochlear stimulator, the signal processing unit comprising a port and further configured to generate the one or more stimulation parameters; and
   one or more electrodes configured to be removably coupled directly to the port of said signal processing unit;
   wherein said signal processing unit is configured to use said one or more electrodes removably coupled directly to said port of said signal processing unit to detect said one or more central auditory potentials and wherein said signal processing unit is configured to process said detected one or more central auditory potentials.

2. The system of claim 1, wherein said signal processing unit is further configured to adjust one or more of said stimulation parameters in accordance with said detected one or more central auditory potentials.

3. The system of claim 1, wherein said one or more electrodes removably coupled directly to said port of said signal processing unit comprise:
   a first electrode configured to serve as a sensing electrode; and
   a second electrode configured to serve as a reference electrode.

4. The system of claim 1, wherein said signal processing unit comprises:
a microphone configured to detect one or more acoustic signals; and
circuitry configured to process said detected one or more acoustic signals;
wherein said circuitry is further configured to process said detected one or more central auditory potentials.

5. The system of claim 4, wherein said circuitry comprises at least one of an amplifier and a processor.

6. The system of claim 1, wherein said cochlear stimulator is configured to synchronize said generation of said stimulation current with said detection of said one or more central auditory potentials.

7. The system of claim 1, wherein said signal processing unit comprises a behind-the-ear processing unit.

8. The system of claim 1, wherein said signal processing unit comprises a hearing aid.

9. A method of detecting one or more central auditory potentials, said method comprising:
implanting a cochlear stimulator fully within a patient;
generating and applying a stimulation current by way of one or more electrodes implanted within a cochlea of said patient in accordance with one or more stimulation parameters with the cochlear stimulator;
providing a signal processing unit housed within a single casing and comprising a port and configured to be located external to said patient and communicatively coupled to said implantable cochlear stimulator;
generating the one or more stimulation parameters with the signal processing unit;
removably coupling one or more electrodes directly to the port of said signal processing unit, the one or more electrodes being located external to the patient;
detecting one or more central auditory potentials with said signal processing unit by way of said one or more electrodes; and
processing said detected one or more central auditory potentials with said signal processing unit.

10. The method of claim 9, further comprising adjusting, by the signal processing unit, one or more of said stimulation parameters in accordance with said detected one or more central auditory potentials.

11. The method of claim 9, wherein said one or more electrodes removably coupled directly to said port of said signal processing unit comprise:
a first electrode configured to serve as a sensing electrode; and
a second electrode configured to serve as a reference electrode.

12. The method of claim 9, further comprising:
detecting one or more acoustic signals with said signal processing unit; and
processing said one or more detected acoustic signals with said signal processing unit.

13. The method of claim 9, further comprising synchronizing said generation of said stimulation current with said detection of said one or more central auditory potentials.

* * * * *